United States Patent [19]

Leach

[11] 4,269,735
[45] May 26, 1981

[54] MAGNESIUM OXIDE CATALYST
[75] Inventor: Bruce E. Leach, Ponca City, Okla.
[73] Assignee: Conoco, Inc., Ponca City, Okla.
[21] Appl. No.: 113,991
[22] Filed: Jan. 21, 1980
[51] Int. Cl.³ .................. B01J 27/02; B01J 21/18; B01J 29/00
[52] U.S. Cl. .................................. 252/440; 252/446; 252/457
[58] Field of Search .................................. 252/440
[56] References Cited

U.S. PATENT DOCUMENTS

| | | | |
|---|---|---|---|
| 3,446,856 | 5/1969 | Hamilton | 568/804 X |
| 3,479,410 | 11/1969 | Hamilton | 568/804 |
| 3,873,628 | 3/1975 | Van Sorge | 568/743 X |
| 3,893,948 | 7/1975 | Khachik et al. | 252/440 |
| 3,968,172 | 7/1976 | Ichikawa et al. | 260/621 R |
| 4,060,560 | 11/1977 | Leach | 568/805 |
| 4,060,561 | 11/1977 | Starks | 568/763 |
| 4,110,253 | 8/1978 | Leach | 568/804 X |
| 4,125,736 | 11/1978 | Leach | 568/804 |

FOREIGN PATENT DOCUMENTS 5377029 12/1976 Japan.

Primary Examiner—Delbert E. Gantz
Assistant Examiner—William G. Wright
Attorney, Agent, or Firm—Cortlan R. Schupbach, Jr.

[57] ABSTRACT

Amorphorus titanium, uranium, chromium ions and zirconium together with sulfate ions are effective promoters for magnesium oxide catalysts. These catalysts are active for the ortho methylation of phenols in the vapor phase to yield 2,6-xylenol.

5 Claims, No Drawings

MAGNESIUM OXIDE CATALYST

This invention comprises an improved catalyst for phenolics alkylation. More specifically, this invention comprises a catalyst and a process. The catalyst is magnesium oxide promoted by selected metal ions and sulfate ions. The catalyst is useful in highly selective phenolic methylation reactions.

Vapor phase methylation of phenols or magnesium oxide is taught in U.S. Pat. No. 3,479,410 which also requires the presence of 2,4,6-trimethylphenol as an ingredient in the feedstream. The invention is useful for phenols having at least one ortho hydrogen. Japanese publication No. 69-27367 teaches phenol methylation over magnesium oxide catalyst in the presence of an elemental metal such as copper, zinc, molybdenum, tungsten, platinum, and palladium.

In addition, U.S. Pat. Nos. 4,060,561 and 4,060,560 teach various reactions over magnesium oxide catalysts promoted with oxides of aluminum, uranium, titanium, cerium, manganese, zinc and iron under specific reaction conditions. U.S. Pat. Nos. 4,110,253 and 4,125,736 teach the use of magnesium oxide catalyst promoted with tungsten oxide, silica sol, and sodium silicate for the disproportionation of highly alkylated phenols with phenol.

These catalysts, while useful for many reactions, still produce large amounts of various alkylated by-products which are undesirable in many reactions.

There are many catalysts which teach ortho methylated products from the methylation of phenol in the vapor phase. Magnesium oxide itself is a useful catalyst as set forth in U.S. Pat. No. 3,446,856, but requires temperatures in the range of 457° to 600° C. In this temperature range, catalyst life is short and methanol decomposition is high. Manganese sulfate on magnesium oxide has been used for a catalyst and overcomes the objections mentioned for magnesium oxide alone as shown in U.S. Pat. No. 3,873,628. Titanium oxide is known as a catalyst for phenol methylation as set forth in Japan Kokai No. 78 77,029. Selectivity is shown to be good using a 1/0.05 magnesium oxide/titanium dioxide catalyst. The present invention shows a more active catalyst than the oxides of this reference.

In U.S. Pat. No. 3,873,628, manganese sulfate is mixed with magnesium oxide resulting in a catalyst which is an ortho director when an alkyl alcohol is reacted with a phenolic compound. The combination is said to allow the alkylation to proceed at a lower temperature without reducing selectivity to the ortho position. However, the reaction produces sulfur dioxide as a by-product and must be removed before disposal in the atmosphere.

Chromium oxide alone as a promoter with magnesium oxide, has also been described in Japan Kokai No. 79/30,122 and Japan Kokai No. 79 27,529, respectively. The chromium oxide on magnesium oxide catalyst described is more active and decomposes less methanol than a corresponding chromium oxide/magnesium oxide catalyst for any given temperature. Uranium oxide/magnesium oxide has also been described in Chem Abstracts 67:73341.

Thus it is clear that the prior art catalysts, while useful for various reactions, have hitherto not been sufficiently reactive, do not develop sufficiently high surface area and crush strength necessary for the conditions of these reactions. Most reactions using these catalysts are carried out at such high temperatures that catalyst life is short while product and feedstream decomposition is high. It would therefore be of great benefit to provide an improved catalyst and process that overcomes these rejections.

It has now been discovered in accordance with the present invention that a catalyst sufficiently active for methylation of phenols and which operates at low temperatures with accompanying low decomposition of alkylating agent can be obtained by adding to a magnesium oxide base catalyst from about 0.05 to about 15% by weight of a promoter selected from the group consisting of amorphous titanium, uranium, zicronium or chromium ions together with sulfate ions at temperatures of 0.05 to about 15% by weight, and mixtures of these, all based on the total weight of the final catalyst. Surprisingly, this catalyst does not effectively disproportionate phenol materials.

In addition the catalysts of the present invention can optionally contain up to about 3% by weight of graphite as a pelletizing lubricant. The graphite has no significant effect on product distribution.

The materials produced using the catalyst and process of the instant invention are useful as modifiers for phenol formaldehyde resins, as chemical intermediates to phenol derivatives in the synthesis of Vitamin E and in polymerization processes such as the preparation of polyphenyleneoxide (PPO), a high performance thermoplastic.

The catalysts of the present invention are formed using special preparations. In addition to the catalysts found to be effective in the present invention, many other catalysts were tested. In general, catalysts were prepared by dissolving 2.8 grams of metal sulfate in about 12 cubic centimeters (cc) of water. The solution was then added to 25 grams (g) of magnesium oxide catalyst (Harshaw MG-0601, trademark of and sold by Harshaw Chemical Company), the solution evaporated to dryness and then calcined in air for two hours at about 500° C.

However, not all sulfates are water soluble and special preparations were required for titanium, zirconium, uranium, molybdenum, cerium, vanadium, and tin which were tested.

Vanadium sulfate promoted catalyst was obtained by forming a solution of $VO(C_2O_4)_2{}^{-2}$ and $(NH_4)_2SO_4$ by simple mixing. This mixture was then added to magnesium oxide and the balance of the procedure was carried out.

Titanium sulfate promoted catalyst was prepared by diluting 3 cubic centimeters (cc) of tetraisopropyl titanate to 10 cc volume with ispropanol. This solution was added to magnesium oxide and the solvent removed under vacuum. An ammonia sulfate $(NH_4)_2 SO_4$ solution was added to incorporate sulfate anion, followed by drying and calcination.

Molybdenum sulfate promoted catalyst was prepared by dissolving molybdenum trioxide ($MoO_3$) in aqueous $NH_3$ and adding the solution to magnesium oxide. After drying, a solution of ammonia sulfate $(NH_4)_2 SO_4$ was added, followed by drying and calcination.

Zirconium sulfate promoted catalyst was prepared by adding sulfuric acid to zirconium sulfate to increase the solubility of $ZrOSO_4$ before impregnation of magnesium oxide.

Uranium sulfate promoted catalyst was prepared by dissolving uranium nitrate in water and adding the solution to magnesium oxide. The mixture was dried and ammonium sulfate was added. The catalyst was formed by the subsequent drying and calcination step described.

Tin sulfate promoted catalyst was prepared by dissolving stannous chloride ($SnCl_2$) in ammonia sulfate solution, adding to magnesium oxide, drying and calcining.

Cerium sulfate promoted catalyst was prepared by the same method described for uranium, using cerium nitrate.

These preparations of the catalysts of the instant invention are not the only ones possible, and are used simply to illustrate methods which can be used. It is apparent from data obtained that most metal sulfates are not effective catalysts, and in fact, most are poor catalysts.

The invention is more concretely described with reference to the examples below wherein all parts and percentages are by weight unless otherwise specified. The examples are provided to illustrate the present invention and not to limit it.

EXAMPLE 1

The Catalyst

The catalyst is magnesium oxide base promoted with $Ti^{+4}$ and sulfate ions. The magnesium oxide carrier is a high surface area magnesium oxide (such as Merck Maglite D). Various sources of sulfate ion are possible, but one preferred component is magnesium sulfate. Titanium is well dispersed in the catalyst and the X-ray analysis does not reveal any well crystallized titanium compounds. Magnesium oxide is treated with a small amount of ispropanol followed by addition of titanium tetraisopropoxide diluted with isopropanol. Any method of titanium tetraisopropoxide addition which creates a good dispersion on the magnesium oxide surface will produce a selective catalyst.

Catalyst Preparation

While various preparations are possible for the above described catalyst, the following procedure is preferred. The raw materials (on a 100 part by weight basis) necessary are:

| | | |
|---|---|---|
| Magnesium oxide | 77.8 parts | |
| Titanium tetraisopropoxide | 6.5 parts | |
| Magnesium sulfate | 5.4 parts | |
| Graphite | 1.7 parts | |
| Silica sol | 8.6 parts | 30% aqueous solution |

In preparing the catalyst, magnesium oxide is treated with titanium tetraisoproxide before any aqueous additions. X-ray analysis is used to evaluate success. The silica sol is added as a 30 weight percent solution. Magnesium sulfate is added as an aqueous solution. Water content is adjusted as desired for tableting (3/16" diameter tablets are commerical size). Surface area of the final material falls in the range of 80–150 $m^2/g$. The tablets were calcined in air at 500° C. for 3 hours.

The catalyst operated continuously for 19 days or 456 hours. No deactivation was noticed at the conclusion of the test. The final run was a high conversion phenol methylation. The final 72 hour product was collected and distilled. Analysis by gas/liquid chromatography is given below in weight percent (w/o).

TABLE 1

| Composition | Feed | Product |
|---|---|---|
| Methanol | 57.27 | 35.93 |
| Water | 9.09 | 16.87 |
| Anisole | | 0.08 |
| Phenol | 33.64 | 2.30 |
| o-Methylanisole | | 0.20 |
| o-Cresol | | 10.66 |
| m,p-Cresol + 2,6-Dimethylanisole | | 0.25 |
| 2,6-Xylenol | | 29.98 |
| 2,4-Xylenol | | 0.66 |
| 2,4,6-Trimethylanisole | | 0.14 |
| 2,4,6-Trimethylphenol | | 2.74 |
| 2,3,6-Trimethylphenol | | 0.16 |
| High Boilers | | 0.03 |
| | | 100.00 |

Conditions: LHSV=1.4, 470° C., 20 PSIG

EXAMPLE 2

A run was made with the preferred catalyst using recycle methanol. Reaction conditions were 468° C., LHSV=2.0 and 20 PSIG. The results are set forth in Table 2.

TABLE 2

| Composition | Feed | Product |
|---|---|---|
| Methanol | 57.27 | 33.47 |
| Water | 9.09 | 16.42 |
| Anisole | | 0.16 |
| Phenol | 33.64 | 4.22 |
| o-Methylanisole | | 0.27 |
| o-Cresol | | 13.63 |
| m,p-Cresol + 2,6-Dimethylanisole | | 0.32 |
| 2,6-Xylenol | | 27.66 |
| 2,4-Xylenol | | 1.01 |
| 2,4,6-Trimethylanisole | | 0.15 |
| 2,4,6-Trimethylphenol | | 2.52 |
| 2,3,6-Trimethylphenol | | 0.15 |
| High Boilers | | 0.02 |

Initially the temperature and space velocity must be controlled to achieve good selectivity. However, 2,4,6-trimethylphenol output rapidly decreases.

EXAMPLE 3

Example 3 was carried out to show the effect of varying times and conditions using a standard feed of 56.57 percent methanol, 9.10 percent water, 25.75 percent phenol and 8.58 percent o-cresol. The reactor was at atmospheric pressure. The results are set forth in Table 3.

TABLE 3

| Time, hours | 16 | 45 | 87 | 208 |
|---|---|---|---|---|
| °C. | 443 | 462 | 462 | 464 |
| LHSV | 2.0 | 2.0 | 2.0 | 1.4 |
| Product Composition | | | | |
| Anisole | 0.81 | 0.44 | 0.23 | 0.17 |
| Phenol | 23.94 | 12.35 | 11.11 | 16.21 |
| o-Methylanisole | 0.63 | 0.58 | 0.41 | 0.22 |
| o-Cresol | 44.99 | 34.90 | 31.75 | 37.50 |
| m,p-Cresol | Tr | 0.75 | 0.62 | 0.37 |
| 2,6-Dimethylanisole | | | | |
| 2,6-Xylenol | 22.90 | 43.94 | 49.81 | 42.46 |
| 2,4-Xylenol | 3.63 | 1.89 | 1.37 | 0.96 |
| 2,4,6-Trimethylanisole | Tr | 0.21 | 0.22 | 0.11 |
| 2,4,6-Trimethylphenol | 2.89 | 4.61 | 4.28 | 1.90 |
| 2,3,6-Trimethylphenol | 0.21 | 0.28 | 0.20 | 0.10 |
| High Boilers | Tr | 0.05 | Tr | Tr |

EXAMPLE 4

A silica-free catalyst was prepared using 180 g magnesium oxide powder (Merck Maglite D), 15 g titanium tetraisopropoxide and 6.25 g $MgSO_4$. Surface area of the tabletted and calcined (500° C., 2 hrs.) catalyst was 116 $m^2/g$. The catalyst had a lower crush strength than catalysts prepared with silica having similar ingredients. Analysis of the reaction product at 465° C. reaction temperature, 1.4 LHSV, 20 psig is given in table 4. The feed was a 5:1 mole ratio of methanol to phenolics containing 9.1% water.

TABLE 4

| Cresylics Composition | Feed | Product |
|---|---|---|
| Anisole | | 0.79 |
| Phenol | 75 | 4.32 |
| o-Methylanisole | | 0.55 |
| o-Cresol | 25 | 41.07 |
| m,p-Cresol + 2,6-Dimethylphenol | | 0.42 |
| 2,6-Xylenol | | 43.71 |
| 2,4-Xylenol | | 3.34 |
| 2,4,6-Trimethylphenol | | 5.54 |
| 2,3,6-Trimethylphenol | | 0.26 |

EXAMPLE 5

An experiment was carried out to illustrate the effect of higher titanium and magnesium sulfate levels. The catalyst was prepared as previously described except the composition of the catalyst was changed compared to the previous examples (100 part by weight basis).

| | |
|---|---|
| magnesium oxide | 70.9 parts |
| magnesium sulfate | 9.8 parts |
| titanium tetraisopropoxide | 9.8 parts |
| silica sol | 7.9 parts |
| graphite | 1.6 parts |

The surface area of the catalyst was 128 $m^2/g$. Results were compared at 16 and 48 hours. Differences between Example 5 and Example 1 were apparent. Example 5 produced higher anisole and 2,4,6-trimethylphenol levels which are undesirable. The feed composition was 56.57 percent methanol, 9.10 percent water 25.75 percent phenol and 8.58 percent o-cresol. The reaction was carried out at an LHSV of 2.0 and temperature of 456° C. The results are set forth in Table 5.

TABLE 5

| Cresylics Composition | 16 hrs. | 48 hrs. |
|---|---|---|
| Anisole | 1.17 | 2.97 |
| Phenol | 18.58 | 22.06 |
| o-Methylanisole | 0.94 | 1.85 |
| o-Cresol | 38.90 | 37.73 |
| 2,6-Dimethylanisole + m,p-Cresol | 1.52 | 2.34 |
| 2,6-Xylenol | 27.73 | 25.53 |
| 2,4-Xylenol | 3.28 | 2.52 |
| 2,4,6-Trimethylanisole | 0.60 | 0.60 |
| 2,4,6-Trimethylphenol | 6.74 | 4.06 |
| 2,3,6-Trimethylphenol | 0.38 | 0.32 |
| High Boilers | 0.17 | Tr |
| | 100.00 | 100.00 |

EXAMPLE 6

An example was carried out to illustrate the effect of various levels of $(NH_4)_2SO_4$ [ammonium sulfate].

Magnesium oxide powder (180 g) was mixed with 40–60 g isopropanol. Titanium tetraisopropoxide (25 g) was added to the MgO and well mixed. Silica sol in 30% aqueous solution and varying amounts of ammonium sulfate were added.

The water content was adjusted by drying and graphite added before tableting. All catalysts were calcined 2 hours at 500° C. in air prior to use. Three cases were studied.

Case 1  4 g $(NH_4)_2SO_4$
Case 2  16 g $(NH_4)_2SO_4$
Case 3  25 g $(NH_4)_2SO_4$ A very small amount of dimethyl sulfide was detected in the reactor effluent. More dimethyl sulfide is observed when ammonium sulfate is used than when magnesium sulfate is used. Also ammonium sulfate has the disadvantage that ammonia is released when the ammonium sulfate is added to the magnesium oxide-titanium tetraisopropoxide mixture. The results of this experiment are set forth in Table 6.

TABLE 6

| | Feed | Product Case 1 | Case 2 | Case 3 |
|---|---|---|---|---|
| Temperature °C. | | 465 | 465 | 468 |
| Pressure, PSIG | | 40 | 30 | 40 |
| LHSV | | 1.2 | 1.2 | 1.4 |
| Methanol | 56.57 | Approx. 40 percent | | |
| Water | 9.10 | Approx. 16 percent | | |
| Phenolics Distribution, w/o | | | | |
| Anisole | | 1.78 | 2.39 | 0.44 |
| Phenol | 75.00 | 18.35 | 4.14 | 1.40 |
| o-Methylanisole | | 0.64 | 1.42 | 0.45 |
| o-Cresol | 25.00 | 53.37 | 39.85 | 30.89 |
| m,p-Cresol + 2,6-Dimethyl-anisole | | 1.04 | 0.72 | 0.31 |
| 2,6-Xylenol | | 20.84 | 41.29 | 62.16 |
| 2,4-Xylenol | | 2.65 | 4.62 | 1.18 |
| 2,4,6-Trimethylanisole | | 0.08 | 0.16 | 0.06 |
| 2,4,6-Trimethylphenol | | 1.15 | 4.22 | 2.94 |
| 2,3,6-Trimethylphenol | | 0.20 | 0.71 | 0.14 |
| High Boilers | | Tr | 0.48 | 0.03 |

EXAMPLE 7

An experiment was carried out to determine the effect of sodium on the catalyst composition using the following ingredients:

90 g Merck Maglite D magnesium oxide powder
12 g titanium tetraisopropoxide
2 g sodium sulfate
3 g sodium silicate
2 g graphite The catalyst was prepared following the procedures outlined previously. The order of addition was magnesium oxide, titanium tetraisopropoxide, sodium sulfate, sodium silicate and graphite. The catalyst was tabletted and calcined in air at 500° C. for 2 hours. As table 7 shows, the conversion to 2,6-xylenol is impeded by this catalyst composition. Anisoles were also very high.

| Reaction Conditions | Feed - 5/1 mole ratio methanol/cresylics with 9.1% $H_2O$. |
|---|---|
| Temperature | 462° C. |
| LHSV | 1.4 |

TABLE 7

| Cresylics Composition | Feed | Product |
|---|---|---|
| Anisole | | 4.20 |

TABLE 7-continued

| Cresylics Composition | Feed | Product |
|---|---|---|
| Phenol | 75 | 11.15 |
| o-Methylanisole | | 2.88 |
| o-Cresol | 25 | 45.02 |
| m,p-Cresol + 2,6-Dimethylanisole | | 1.65 |
| 2,6-Xylenol | | 25.23 |
| 2,4-Xylenol | | 6.08 |
| 2,4,6-Trimethylphenol | | 3.79 |

EXAMPLE 8

An experiment was carried out to show the effect of replacing MgSO$_4$ with CaSO$_4$. The catalyst was prepared by mixing 180 g magnesium oxide (Merck Maglite D) with 20 cc isopropanol. The treated magnesium oxide was sprayed with a solution of 15 cc titanium tetraisopropoxide in 15 cc of isopropanol during constant mixing of the magnesium oxide. CaSO$_4$.2H$_2$O (17.9 g) was added followed by 20 g of a 30% aqueous solution of silica sol. The mixture was dried, sieved and tableted. The catalyst was calcined 2 hours at 500° C. The catalyst (15 cc) was loaded into a ½" diameter electrically heated stainless steel reactor. The feedstock for the reaction and the product are described in table 8. The catalyst is not quite as active or selective as catalysts prepared using MgSO$_4$ in place of CaSO$_4$.

TABLE 8

2,6-Xylenol Synthesis Using a CaSO$_4$ Promoted Ti$^{+4}$/MgO Catalyst

| | Feed | | | | |
|---|---|---|---|---|---|
| Hrs, Culm | | 23 | 30 | 70 | 94 |
| Temperature, °C. | | 465 | 462 | 460 | 465 |
| Pressure, PSIG | | 20 | 25 | 40 | 40 |
| LHSV | | 1.4 | 1.8 | 1.4 | 1.4 |
| Composition, Cresylics - w/% | | | | | |
| Anisole | | 0.81 | 0.76 | 0.72 | 0.73 |
| Phenol | 75 | 8.69 | 20.49 | 21.77 | 18.12 |
| o-Methylanisole | | 1.17 | 0.72 | 0.69 | 0.78 |
| o-Cresol | 25 | 21.35 | 37.85 | 37.28 | 39.07 |
| m,p-Cresol, 2,6-Dimethylanisole | | 1.38 | 1.07 | 0.91 | 0.83 |
| 2,6-Xylenol | | 45.23 | 28.34 | 31.16 | 32.99 |
| 2,4-Xylenol | | 3.41 | 4.05 | 2.70 | 2.82 |
| 2,4,6-Trimethylanisole | | 0.39 | 0.13 | Tr | Tr |
| 2,4,6-Trimethylphenol | | 16.71 | 6.14 | 4.70 | 4.34 |
| 2,3,6-Trimethylphenol | | 0.48 | 0.19 | Tr | Tr |
| High Boilers | | 0.38 | 0.26 | 0.07 | 0.32 |
| | | 100.00 | 100.00 | | |

[1]Feed contains 9.10 w/% H$_2$O in addition to 56.57 w/% methanol, cresylics are 34.33 w% of sample

EXAMPLES 9-22

Various metal sulfates were evaluated at standardized conditions of 460° C., 1 LHSV atmospheric pressure and a 5 to 1 methanol to phenol mole ratio. The feed contained 9% weight water and was passed over catalysts containing 2.8 gram metal sulfate per 25 gram magnesium oxide catalyst. A wide range of metal sulfate promoters for magnesium oxide catalysts were tested. In carrying out the tests, it was considered desirable to make ortho cresol and 2,6-xylenol. Mixtures containing 2,4-xylenol, 2,4,6-trimethylphenol and higher boiling components were considered undesirable.

A summary of results from these direct comparisons are set forth in Table 9 below.

TABLE 9

METAL SULFATES EVALUATED FOR PHENOL METHYLATION

| Metal | Example | Comments |
|---|---|---|
| Magnesium | 9 | Poor selectivity, rapid deactivation |
| Titanium | 2 | High activity and good selectivity |
| Vanadium | 10 | High methanol decomposition |
| Chromium | 23 | High selectivity, good activity |
| Manganese | 11 | U.S. Pat. No. 3,873,628 |
| Iron | 12 | Rapid deactivation in 20 hours |
| Cobalt | 13 | Poor selectivity, rapid activity decline |
| Nickel | 14 | Poor activity |
| Copper | 15 | Poor activity |
| Zinc | 16 | Poor activity |
| Zirconium | 17 | Fair activity, good selectivity |
| Molybdenum | 18 | Rapid deactivation 16 hours |
| Cerium | 19 | High methanol decomposition |
| Uranium | 22 | Good activity and selectivity |
| Tin | 20 | Low conversion |

It is readily apparent that a wide range of results are obtained using various metal sulfates.

The feedstock for all evaluations was the same. Methanol mole ratio was 5 to 1 methanol to phenol. Water content of the feed was 9.1% to extend catalyst life. Unless otherwise stated, the magnesium oxide was in the form of ⅛ inch diameter tablets. The tests utilized a commerically available magnesium oxide (Harshaw MG-0601-T, product of the Harshaw Chemical Company). The feed was vaporized in a preheated segment of ⅛ inch line and passed over the catalyst at 1.0 liquid hourly space velocity (LHSV) at 460° C. The product was analyzed for phenolic content by gas liquid chromatography (GLC). Gas evolution was measured as representative of methanol decomposition in the reactor.

EXAMPLE 9

Magnesium sulfate was used as the source of sulfate ion. The initial product was primarily 2,4,6-trimethylphenol and the activity decreased rapidly overnight (17 hours). The results are shown in Table 10.

TABLE 10

| Cresylics Composition, w/o | 1 hr | 17 hrs |
|---|---|---|
| Anisole | 2.18 | 1.73 |
| Phenol | 31.52 | 57.81 |
| o-Methylanisole | 1.11 | 0.57 |
| o-Cresol | 9.46 | 11.93 |
| 2,6-Dimethylanisole | 1.73 | 0.60 |
| m,p-Cresol | | |
| 2,6-Xylenol | 18.66 | 12.29 |
| 2,4-Xylenol | 4.10 | 2.54 |
| 2,4,6-Trimethylanisole | 1.66 | 0.25 |
| 2,4,6-Trimethylphenol | 26.53 | 11.86 |
| 2,3,6-Trimethylphenol | 0.79 | 0.11 |
| High Boilers | 2.26 | 0.31 |

EXAMPLE 10

A catalyst was prepared with vanadium ions and tested in the standard run. Results are shown in Table 11.

TABLE 11

| Cresylics Composition, w/o | 1 hr. | 17 hrs |
|---|---|---|
| Anisole | 0.78 | 0.09 |
| Phenol | 3.90 | 80.32 |
| o-Methylanisole | 0.29 | Tr |
| o-Cresol | 13.16 | 17.92 |
| 2,6-Dimethylanisole | 0.34 | Tr |
| m,p-Cresol | | |

TABLE 11-continued

| Cresylics Composition, w/o | 1 hr. | 17 hrs |
|---|---|---|
| 2,6-Xylenol | 51.22 | 1.67 |
| 2,4-Sylenol | 2.22 | |
| 2,4,6-Trimethylanisole | 0.38 | |
| 2,4,6-Trimethylphenol | 26.74 | |
| 2,3,6-Trimethylphenol | 0.26 | |
| High Boilers | 0.71 | |

Methanol decomposition observed was 100 cc of gas in 15 min.

EXAMPLE 11

Manganese ions were tested experimentally in the test reaction. Results are shown in Table 12.

TABLE 12

| Cresylics Composition, w/o | 100 hrs. |
|---|---|
| Anisole | 0.39 |
| Phenol | 24.13 |
| o-Methylanisole | 0.06 |
| o-Cresol | 25.36 |
| m,p-Cresol | 0.11 |
| 2,6-Dimethylanisole | |
| 2,6-Xylenol | 45.92 |
| 2,4-Xylenol | 0.44 |
| 2,4,6-Trimethylanisole | 0.10 |
| 2,4,6-Trimethylphenol | 3.49 |
| | 100.00 |

EXAMPLE 12

Iron ions were tested in the standardized test. Results are set forth in table 13.

TABLE 13

| Cresylics Composition, w/o | 2.5 hrs. | 24 hrs. |
|---|---|---|
| Anisole | 1.38 | 0.51 |
| Phenol | 13.27 | 73.13 |
| o-Methylanisole | 0.46 | Tr |
| o-Cresol | 37.94 | 23.69 |
| m,p-Cresol | 0.33 | Tr |
| 2,6-Dimethylanisole | | |
| 2,6-Xylenol | 36.16 | 2.39 |
| 2,4-Xylenol | 3.65 | Tr |
| 2,4,6-Trimethylanisole | Tr | Tr |
| 2,4,6-Trimethylphenol | 6.68 | 0.23 |
| 2,3,6-Trimethylphenol | 0.13 | Tr |
| High Boilers | Tr | 0.05 |

EXAMPLE 13

Cobalt ions were tested experimentally under the standardized conditions. The results are set forth in Table 14.

TABLE 14

| Cresylics Composition w/o | 2.5 hrs. | 20 hrs. |
|---|---|---|
| Anisole | 1.47 | 0.49 |
| Phenol | 8.09 | 62.24 |
| o-Methylanisole | 1.22 | Tr |
| o-Cresol | 17.51 | 31.67 |
| m,p-Cresol + 2,6-Dimethylanisole | 1.23 | Tr |
| 2,6-Xylenol | 44.32 | 5.25 |
| 2,4-Xylenol | 2.08 | Tr |
| 2,4,6-Trimethylanisole | 0.77 | Tr |
| 2,4,6-Trimethylphenol | 21.42 | 0.25 |
| 2,3,6-Trimethylphenol | 0.82 | 0.10 |
| High Boilers | 1.08 | Tr |

Nickel ions were tested experimentally under standard conditions. The results are set forth in Table 15.

TABLE 15

| Cresylics Composition, w/o | 2 hrs. | 20 hrs. |
|---|---|---|
| Anisole | 1.77 | 0.28 |
| Phenol | 43.01 | 71.27 |
| o-Methylanisole | 0.88 | Tr |
| o-Cresol | 9.37 | 26.01 |
| 2,6-Dimethylanisole + m,p-Cresol | 2.32 | Tr |
| 2,6-Xylenol | 22.24 | 2.34 |
| 2,4-Xylenol | 2.20 | 0.10 |
| 2,4,6-Trimethylanisole | 0.79 | Tr |
| 2,4,6-Trimethylphenol | 15.74 | Tr |
| 2,3,6-Trimethylphenol | 0.67 | Tr |
| High Boilers | 0.93 | Tr |
| | 100.00 | 100.00 |

EXAMPLE 15

Copper ions were tested experimentally in the standard test conditions. The results are set forth in Table 16.

TABLE 16

| Cresylics Composition, w/o | 1 hr. | 4 hrs. |
|---|---|---|
| Anisole | 1.12 | 0.86 |
| Phenol | 32.83 | 53.76 |
| o-Methylanisole | 0.28 | Tr |
| o-Cresol | 38.80 | 36.38 |
| 2,6-Dimethylanisole | 0.25 | 0.10 |
| m,p-Cresol | | |
| 2,6-Xylenol | 21.63 | 7.78 |
| 2,4-Xylenol | 2.35 | 0.79 |
| 2,4,6-Trimethylanisole | Tr | Tr |
| 2,4,6-Trimethylphenol | 2.66 | 0.33 |
| 2,3,6-Trimethylphenol | 0.08 | Tr |
| High Boilers | Tr | Tr |
| | 100.00 | 100.00 |

EXAMPLE 16

Zinc ions were tested under standard conditions. The results are set forth in Table 17.

TABLE 17

| Cresylics Composition, w/o | 16 hrs. |
|---|---|
| Anisole | 0.47 |
| Phenol | 73.72 |
| o-Methylanisole | Tr |
| o-Cresol | 23.97 |
| m,p-Cresol + 2,6-Dimethylanisole | Tr |
| 2,6-Xylenol | 1.69 |
| 2,4-Xylenol | Tr |
| 2,4,6-Trimethylanisole | Tr |
| 2,4,6-Trimethylphenol | 0.15 |
| 2,3,6-Trimethylphenol | Tr |
| High Boilers | Tr |

EXAMPLE 17

Zirconium ions were tested under standard conditions. The results were set forth in Table 18.

TABLE 18

| Cresylics Composition, w/o | 4 hrs. | 28 hrs. |
|---|---|---|
| Anisole | 4.61 | 3.32 |
| Phenol | 4.96 | 42.93 |
| o-Methylanisole | 2.65 | 0.29 |
| o-Cresol | 28.47 | 42.94 |
| 2,6-Dimethylanisole | 1.04 | 0.35 |
| m,p-Cresol | | |
| 2,6-Xylenol | 31.21 | 7.56 |
| 2,4-Xylenol | 9.57 | 2.01 |
| 2,4,6-Trimethylanisole | 0.28 | Tr |
| 2,4,6-Trimethylphenol | 15.63 | 0.42 |

TABLE 18-continued

| Cresylics Composition, w/o | 4 hrs. | 28 hrs. |
|---|---|---|
| 2,3,6-Trimethylphenol | 0.90 | 0.10 |
| High Boilers | 0.68 | 0.08 |
| | 100.00 | 100.00 |

EXAMPLE 18

Molybdenum ions were tested under standard conditions. The results are set forth in Table 19.

TABLE 19

| Cresylics Composition, w/o | 2 hrs. | 16 hrs. |
|---|---|---|
| Anisole | 1.11 | 0.28 |
| Phenol | 38.33 | 93.37 |
| o-Methylanisole | 0.44 | Tr |
| o-Cresol | 28.39 | 6.01 |
| m,p-Cresol + 2,6-Dimethylanisole | 0.41 | Tr |
| 2,6-Xylenol | 23.38 | 0.38 |
| 2,4-Xylenol | 1.98 | |
| 2,4,6-Trimethylanisole | 0.19 | |
| 2,4,6-Trimethylphenol | 5.32 | |
| 2,3,6-Trimethylphenol | 0.28 | |
| High Boilers | 0.17 | |
| | 100.00 | 100.00 |

EXAMPLE 19

Cerium ions were tested under standard conditions. The catalyst was prepared containing $Ce_2(SO_4)_3/MgO$. Methanol decomposition as meausred by the volumn of gas evolved from the reactor was 100 ml in 3 minutes. This compares to 100 ml in 30 minutes for the $TiO_2/SO_4^=/MgO$ catalyst described in this invention whereby material balance the methanol decomposition as a percentage of initial methanol was 6 percent. Methanol loss with the cerium catalyst was thus about 50 percent which is highly undesirable.

EXAMPLE 20

Tin ions were tested under standard conditions. The results are shown in Table 20.

TABLE 20

| Cresylics Composition, w/o | 1.5 hrs. | 19 hrs. |
|---|---|---|
| Anisole | 3.10 | 1.42 |
| Phenol | 15.95 | 63.14 |
| o-Methylanisole | 1.16 | Tr |
| o-Cresol | 38.72 | 30.64 |
| 2,6-Dimethylanisole + m,p-Cresol | 0.93 | 0.20 |
| 2,6-Xylenol | 25.36 | 3.26 |
| 2,4-Xylenol | 6.79 | 0.56 |
| 2,4,6-Trimethylanisole | 0.10 | 0.15 |
| 2,4,6-Trimethylphenol | 7.55 | 0.43 |
| 2,3,6-Trimethylphenol | 0.24 | 0.10 |
| High Boilers | 0.10 | 0.10 |
| | 100.00 | 100.00 |

EXAMPLE 21

The titanium sulfate/magnesium oxide catalyst was used in a phenolics methylation using the feedstock and conditions previously described. A typical product obtained on a phenolics only basis is set forth in Table 21. The results are based on GLC analysis.

TABLE 21

| Ti/SO$_4$/MgO Catalyst | |
|---|---|
| Component | w/o |
| Anisole | 1.0 |

TABLE 21-continued

| Ti/SO$_4$/MgO Catalyst | |
|---|---|
| Component | w/o |
| Phenol | 16.8 |
| o-Methylanisole | 0.1 |
| o-Cresol | 49.7 |
| 2,6-Xylenol | 30.1 |
| 2,4-Xylenol | 1.0 |
| 2,4,6-Trimethylphenol | 1.2 |
| Higher Boilers | 0.1 |
| | 100.00 |

This catalyst was operated for approximately 100 hours with no apparent loss in activity.

EXAMPLE 22

The uranium sulfate/magnesium oxide catalyst was prepared as described above. The reaction was carried out using the feedstock and conditions set forth. The phenolics product from the reactor was analyzed using GLC and had the composition set forth in Table 22 below.

TABLE 22

| UO$_2$SO$_4$/MgO Catalyst | |
|---|---|
| Component | W/o |
| Anisole | 0.8 |
| Phenol | 29.1 |
| o-Methylanisole | 0.4 |
| o-Cresol | 36.7 |
| p-Cresol | |
| 2,6-Dimethylanisole | 0.3 |
| 2,6-Xylenol | 28.3 |
| 2,4-Xylenol | 1.7 |
| 2,4,6-Trimethylphenol | 2.3 |
| High Boilers | 0.4 |

EXAMPLE 23

A chromium sulfate/magnesium oxide catalyst was used in a reaction under the standard test conditions set forth above. Phenolics product was again analyzed using GLC. The results are as set forth in Table 23 below.

TABLE 23

| Cr$_2$(SO$_4$)$_3$/MgO Catalyst | |
|---|---|
| Component | w/o |
| Anisole | 1.8 |
| Phenol | 14.3 |
| o-Methylanisole | 0.4 |
| o-Cresol | 46.6 |
| m-p-Cresol | 0.2 |
| 2,6-Xylenol | 27.8 |
| 2,4-Xylenol | 5.0 |
| 2,4,6-Trimethylphenol | 3.8 |
| High Boilers | 0.1 |
| | 100.00 |

EXAMPLE 24

A titanium dioxide/magnesium oxide catalyst was prepared by adding three cubic centimeters tetraiospropyltitanate to 9 cubic centimeters of isopropanol. The mixture is then impregnated on 25 grams of magnesium oxide catalyst (Harshaw MG-0601). The catalyst was then dried and calcined as described for standard conditions set forth above. The catalyst was then used in the standard conditions described above and the product was analyzed using GLC. The results are set forth in Table 24 below.

TABLE 24

| Component | w/o |
|---|---|
| TiO₂/MgO Catalyst | |
| Anisole | 1.9 |
| Phenol | 61.5 |
| o-Cresol | 31.6 |
| m,p-Cresol | 0.5 |
| 2,6-Xylenol | 3.2 |
| 2,4,6-Xylenol | 1.1 |
| 2,4,6-Trimethylphenol | 0.2 |
| | 100.00 |

When compared, the results of Table 24 as contrasted to Table 21, show that the titanium oxide promoted magnesium oxide catalyst is much less active than those of the present invention containing amorphous titanium ions and sulfate ions.

The catalysts disclosed herein give methylation at lower methanol mole ratios with high amounts of ortho cresol, and high amounts of 2,6-xylenol as principle products, and very low amounts of by-products. This product distribution is important because of the ability to make one pass and obtain high proportions of desired products. In contrast, the titanium dioxide/magnesium oxide catalyst set forth in Example 5 gives very little 2,6-xylenol, an important material.

Phenol methylation is carried out at temperatures of from about 420° to about 500° C. (preferred 440°–470° C.) and a LSHV of from about 0.1 to about 10, although 0.5 to about 3.0 is preferred. No pressures above atmospheric are necessary, although the reaction will proceed at higher pressures. Pressures of from atmospheric to 5 atmospheres is preferred. Water added to feed is not necessary during methylation reactions since water is formed during the reaction.

Representative examples of alkylating agents useful in this practice of the present invention are methanol, ethanol, isopropanol, butanol and others known to those skilled in this art. Of these, methanol is preferred because polymerization and degradation do not occur.

Throughout this specification and claims the terminology m,p-cresol is used to indicate a mixture of meta and para-cresol.

While certain embodiments and details have been shown for the purpose of illustrating this invention, it will be apparent to those skilled in this art that various changes and modifications may be made herein without departing from the spirit or scope of the invention.

I claim:

1. A catalyst for the alkylation of phenol and phenolic material, comprising magnesium oxide promoted with from about 0.5% to about 15.0% by weight of amorphous titanium, uranium, zirconium and chromium ions or mixtures of these, together with from about 0.50% to about 15% by weight of sulfate ion, all based on the total weight of the final catalyst.

2. A catalyst as described in claim 1 wherein titanium is used together with magnesium sulfate.

3. A catalyst as described in claim 2 wherein the catalyst contains in addition from about 1% to about 5% by weight of silica.

4. A catalyst as described in claim 3 wherein the catalyst contains from about 1% to about 3% graphite.

5. A catalyst as described in claim 4 wherein the titanium is present in an amount from about 0.5% to about 10% by weight together with equivalent amounts of sulfate.

* * * * *